United States Patent [19]

Won

[11] 4,254,786
[45] Mar. 10, 1981

[54] DENTAL FLOSS HOLDER

[76] Inventor: Se K. Won, 10401 S. Magnolia St., Anaheim, Calif. 92804

[21] Appl. No.: 96,996

[22] Filed: Nov. 23, 1979

[51] Int. Cl.³ .............................................. A61C 15/00
[52] U.S. Cl. .................................................. 132/92 A
[58] Field of Search ...................... 132/92 R, 92 A, 91, 132/90; 32/40

[56] References Cited

U.S. PATENT DOCUMENTS

| 3,746,017 | 7/1973 | Casselman | 132/92 A |
| 3,766,931 | 10/1973 | Fielder | 132/92 A |
| 3,927,687 | 12/1975 | Thierman | 132/92 A |

Primary Examiner—G. E. McNeill

[57] ABSTRACT

A dental floss holder is provided with a slot-headed locking axle on which a spool of floss is mounted. A length of floss is extracted from the spool disposed within the holder and is spanned across two spaced prongs formed on the holder and locked to the axle by being wound about one side of the slotted head before spanning and the other side of the slotted head after spanning. Tension is applied to the spanned floss by rotating the locking axle which is held in position by a ratcheting spring clip to provide a taut span of floss which can be manipulated between the user's teeth.

6 Claims, 4 Drawing Figures

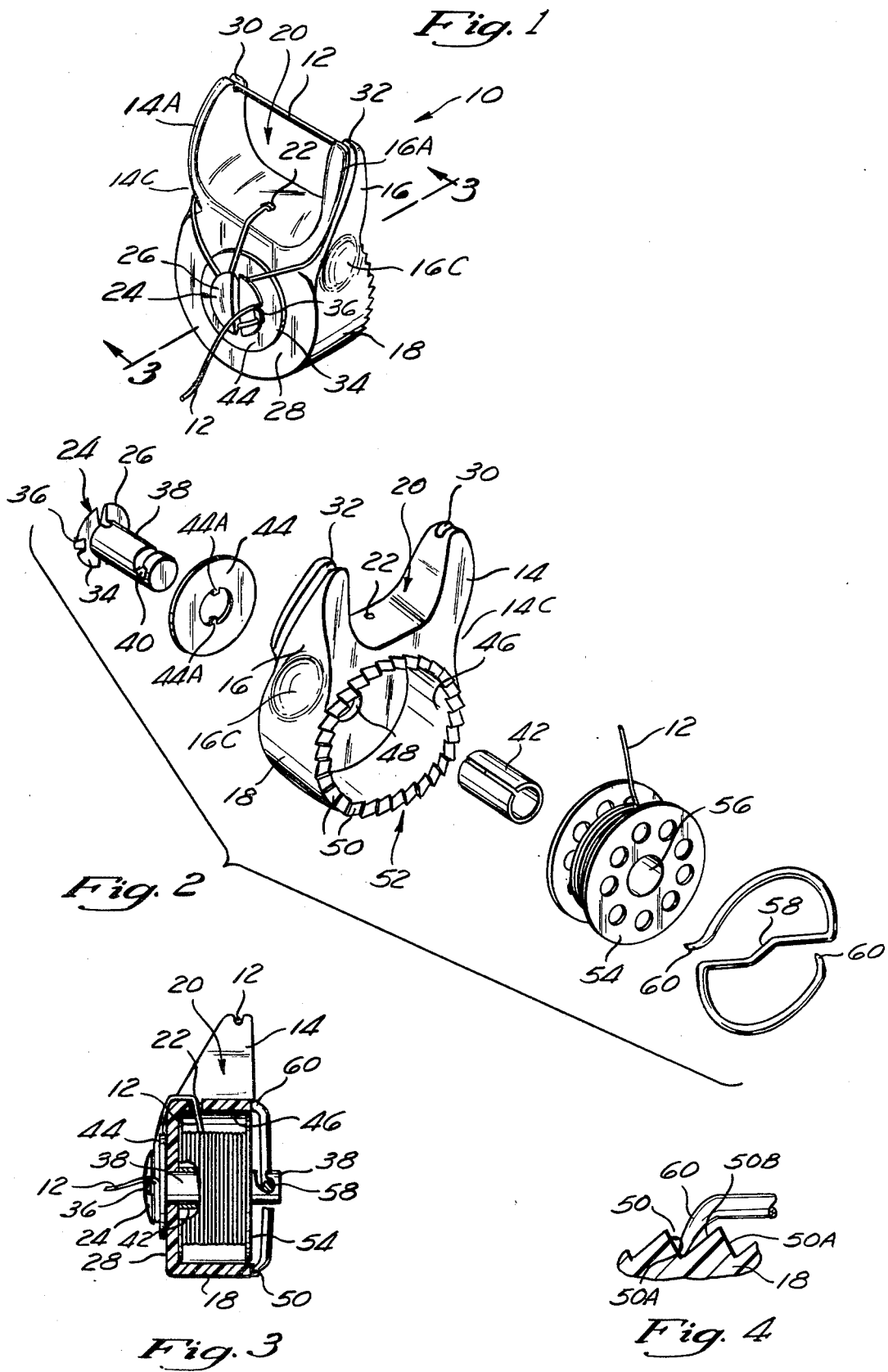

DENTAL FLOSS HOLDER

BRIEF DESCRIPTION OF THE INVENTION

This invention relates to a dental floss holder containing a supply of floss and adapted to provide an exposed section of dental floss maintained under tension for cleaning between the user's teeth. Devices of this type are shown, for example, in U.S. Pat. No. 3,289,681, issued Dec. 6, 1966, O. S. Chambers, inventor; U.S. Pat. No. 3,858,594, issued Jan. 7, 1975, George Ensminger inventor; U.S. Pat. No. 3,993,085, issued Nov. 23, 1975, Edward T. Skinner, inventor; and U.S. Pat. No. 4,004,599, issued Jan. 25, 1977, Marvin L. Rosenfeld, inventor.

In the present invention, a length of floss wound on a spool held within a body member is manually pulled from the spool. When a sufficient length has been unwound, the floss is wound about one side of a slotted head on a locking axle, threaded over two prongs on the holder, and wound about the other side of the slotted head. The locking axle is fixed in position by means of a ratcheting spring clip which engages ratcheting recesses formed in the bottom of the body member. Tension is applied to the floss when stretched between the two prongs by rotation of the locking axle. The taut floss can be manipulated between teeth when the holder is held by the user.

BRIEF DESCRIPTION OF THE DRAWING

The invention may be more readily understood by referring to the accompanying drawing, in which:

FIG. 1 is a perspective view of a dental floss holder according to the present invention;

FIG. 2 is an exploded perspective view thereof;

FIG. 3 is a side elevational view, partly in section, thereof; and

FIG. 4 is a fragmentary sectional view of a portion of the holder ratcheting mechanism.

DETAILED DESCRIPTION

Referring now to FIG. 1, there is shown a perspective view of a dental floss holder 10 illustrating the manner in which dental floss 12 is spanned between a first prong 14 and a second prong 16 of the holder 10. The holder 10 has a body portion 18 which is generally cylindrical and from which the prongs 14 and 16 extend so as to be generally normal thereto, with a space 20 formed therebetween to provide a finger or thumb-receiving accessway to the spanned floss 12, said space being hereinafter referred to as a digit-receiving space. An aperture 22 in the body portion located between the prongs 14 and 16 provides a passageway through which the floss 12 emerges from within the body portion 18. As is seen in FIG. 1, the floss 12 passes from the aperture 22 under a slotted head portion 24 of an axle (see FIG. 3). The floss 12 is passed around one side 26 of the slotted head 24 so as to lock the floss to the head and, from under the head portion 24, the floss 12 passes over a flat top surface 28 of the holder 10 and through a deep slot in the prong 14 which terminates in a prong tip slot 30, through which the floss passes to a similar tip slot 32 formed in the second prong 16. From the tip slot 32, the floss passes through a deep slot 32A formed in the second prong 16 to the top surface 28 of the holder 10 and then under the slotted head 24 around a second portion 34 thereof, which, as is seen in FIG. 1, contains a cutting edge 36 for cutting the excess floss when the desired wrapping has been completed and the excess floss is to be removed. The prongs 14, 16 are generally triangular in cross-section both laterally and longitudinally so that each triangle apex 14A, 16A is on the top side 28 of the holder 10.

Referring now to FIG. 2, there is shown an axle 38 which terminates in the slotted head 24 at one end and, at the other end, has a clip engaging recess 40 formed therein. A cylindrical shim 42 mounts on the axle 38 and is separated from the slotted head 24 by the top surface 28 and a floating flange 44, which is mounted on the axle 38 adjacent the slotted head 24 by a pair of teeth 44A which engage the slotted head slot so as to permit limited axial relative movement between the flange 44 and the slotted head 24. The floss 12 passes and is clamped therebetween. The body portion 18 has a central axial bore 46 formed therein which terminates within the body adjacent its top surface 28 in a smaller aperture 48, which is axially aligned with the central bore 46. At its opposite end, the axial bore 46 opens onto a series of ratcheting recesses 50 formed about the periphery of the body portion 18 at its bottom surface 52. The prongs 14, 16 have flat bases 14B, 16B which lie in the same plane as the bottom surface 52. Dimples 14C, 16C are formed at the junctions of the prongs 14, 16 and the body portion 18 and serve as finger grips for the user. A spool 54 holding the floss 12 is adapted to fit within the axial bore 46. The spool is inserted within the bore 46 and mounted by press-fitting on the axle 38 over the shim 42 so that the axle 38 extends through a central bore 56 in the spool, and the spool is retained in the axial bore 46. As is shown in FIG. 3, a clip 58 engages the clip engaging recess 40 so as to hold the floating flange 44 against the slotted head 24 at the top surface 28. The clip 58, in the preferred embodiment, is an S-shaped clip and has downturned pointed arms 60. As is seen in FIG. 4, the ratcheting recesses are unidirectional in nature, that is, each recess 50 has a stop face 50A and a deflection face 50B. When the clip 58 is engaged in the recess 40, a downturn arm 60 engages the ratcheting recess stop face 50A formed in the periphery of the bottom surface 52. Thus, the ratcheting recesses are unidirectional, that is, they permit ratcheting in one direction only.

Referring now to FIG. 3, there is shown the floss holder 10 partially in section, illustrating the means by which the floss 12 is passed from the axial bore 46 through the aperture 22, so as to permit the floss to exit therefrom and be passed around the slotted head 34 and from the slotted head 34 to the prongs and back to the slotted head, as is shown in FIG. 1. When it is desired to increase the tension on the floss 12 spanned between the prongs 14 and 16, the S-shaped spring clip 58 is rotated manually so as to increase the tension on the floss by winding the floss on the axle 38 between the slotted head 24 and the floating flange 44. In the embodiment shown, rotation of the S-shaped clip spring in a clockwise direction will result in the increase in the desired tension of the floss spanned between the prongs, as the prongs pass freely over the deflection faces 50B in response to such rotation, but are held in position by the stop face 50A when rotation is stopped. In other words, the spring can not be rotated counterclockwise to reduce the tension in the spanned floss.

The dental floss holder 10 of the present invention employs a simple locking arrangement to enable the user to readily lock the spanned floss, thereby permitting a tensioned length of floss to be formed quickly and with a minimum of effort for immediate use. In use, the holder 10 is partially inserted into the mouth of the user so that the prongs 14, 16 are disposed, one to the lingual and one to the labial side of the tooth structure to be cleaned. The floss 12 is then worked between adjacent teeth in order to provide the cleaning function. While the teeth are being so cleaned, increased tension may be supplied by rotation of the S-shaped spring clip as previously described. When the floss has become worn, it is unwound from the slotted head 24 and new floss pulled from the spool 54 and spanned between the prongs 14, 16 and locked by means of the slotted head 24 as previously described. New floss is then available for use in cleaning additional teeth.

I claim:

1. A dental floss holder comprising:

a body member having an axial bore formed therein extending from one side thereof and terminating in an aperture of a smaller diameter opening onto the other body side, said body means having a pair of prongs of generally triangular cross-section extending outwardly laterally from the body member normal to the bore and in the same direction and in generally parallel relationship to one another, each of said prongs having a deep floss receiving groove formed longitudinally along its outer surface remote from the other prong, and each prong terminating in a tip across which the groove extends toward the other prong;

an axle extending through the body member and having a head with a slot formed on one end thereof so as to be disposed adjacent the smaller diameter aperture and a floating flange mounted on the axle and fixed thereto adjacent the slotted head by means of a pair of teeth formed on the flange inner periphery and extending into the head slot at either end thereof;

a spool for holding dental floss mounted on the axle within the body member;

a passageway formed in the body member opening at one end between the prongs and at the other end into the axial bore for passing the floss from the spool through the body member;

a spring clip having downturned pointed arms; and means formed on said axle remote from the slotted head for engaging said clip so that the clip arms engage unidirectional ratcheting recesses formed on said body adjacent the bore;

whereby the axle is normally fixed in position by engagement of the arms and recesses but may be unidirectionally rotated by application of manual rotary pressure to the clip.

2. A dental floss holder comprising:

(a) a body member having a flat top and a flat bottom and an enlarged axial bore formed therein opening in its full diameter onto the bottom and terminating within the body with an axially aligned aperture of a smaller diameter opening onto the top from the bore;

said body member having a plurality of unidirectional ratcheting recesses formed on the bottom peripherally about the bore and a pair of prongs of generally triangular cross-section both laterally and longitudinally extending outwardly laterally from the body member in the same direction and in generally parallel relationship to one another, one side of each of said prongs lying in the same plane as the flat bottom so that said prongs taper generally downwardly and outwardly from the flat top so as to form a digit-receiving space between the prongs;

each of said prongs having a deep floss receiving groove formed longitudinally along its outer surface remote from the other prong, said prongs including said grooves being mirror images of one another and each terminating in a tip across which the respective groove extends toward the other prong;

(b) a spool disposed within the axial bore of the body member for holding dental floss, said spool having a central bore aligned with and larger than the axially aligned aperture in the body member top;

(c) a passageway formed in the body member opening at one end into the digit-receiving space and at the other end into the axial bore for passing the floss from the spool through the body member;

(d) an axle extending through the spool bore and the body member and having a head with a slot on one end thereof external and adjacent the body member axially aligned aperture and a clip engaging recess formed in the other end thereof external of the spool bore;

(e) a floating flange mounted on the axle at the slotted head so as to be disposed between the slotted head and the body member; and (f) a clip having downturned pointed arms, said clip being engaged by said axle clip engaging recess so that the arms engage the ratcheting recesses formed in body member bottom, whereby the axle is normally fixed in position by engagement of the arms and recesses but may be rotated unidirectionally by application of manual rotary pressure to the clip.

3. The dental floss holder of claim 2, and in which the clip is S-shaped so as to form a ratcheting spring when engaged by the axle clip engaging recess.

4. A dental floss holder according to claim 2 or 3, and having a cylindrical shim mounted between the spool and the axle so as to separate the axle from the spool, said shim being of greater diameter than the axially aligned aperture so as to be separated from the floating flange by the body member portion in which the smaller diameter aperture is formed.

5. A dental floss holder according to claim 2 or 3 and in which the body member has a digit-receiving recess formed on the outer surface thereof at the intersection of each prong and the prongs are disposed in the body member so as to form a digit-receiving space therebetween.

6. A dental floss holder according to claim 5 and having a cylindrical shim mounted between the spool and the axle so as to separate the axle from the spool, said shim being of greater diameter than the axially aligned aperture so as to be separated from the floating flange by the body member portion in which the smaller diameter aperture is formed.

* * * * *